United States Patent [19]

Schleisman et al.

[11] Patent Number: 5,567,887
[45] Date of Patent: Oct. 22, 1996

[54] ANHYDROUS AMMONIA GAS SAMPLER AND CONCENTRATION SYSTEM

[75] Inventors: Anthony J. Schleisman, Plano; David S. Bollinger, Grapevine, both of Tex.

[73] Assignee: Texas Instruments Incorporated, Dallas, Tex.

[21] Appl. No.: 509,213

[22] Filed: Jul. 31, 1995

Related U.S. Application Data

[63] Continuation of Ser. No. 209,028, Mar. 10, 1994.

[51] Int. Cl.[6] .................................... B01D 7/00
[52] U.S. Cl. ................. 73/863.12; 73/23.33; 73/23.41; 23/294 R; 585/801
[58] Field of Search ..................... 73/23.2, 23.33, 73/23.41, 863.11, 863.12, 864.33, 864.35, 864.52; 220/901, DIG. 9; 203/47; 202/152, 168, 209, 215, 232, 233, 234, 235; 23/294 R; 585/801

[56] References Cited

U.S. PATENT DOCUMENTS

| | | | |
|---|---|---|---|
| 435,464 | 9/1890 | Stroh et al. | 202/152 |
| 525,858 | 9/1894 | McMahon | 202/232 |
| 950,491 | 3/1910 | Nenzel | 202/152 |
| 1,409,338 | 3/1922 | Fenton | 23/294 R |
| 2,617,272 | 11/1952 | Aicher | 202/233 |
| 3,662,588 | 5/1972 | Emerson et al. | 23/294 R |
| 3,807,185 | 4/1974 | Forg et al. | 62/22 |
| 3,992,159 | 11/1976 | Mitchell | 23/294 R |
| 4,022,592 | 5/1977 | Saaski | 55/189 |
| 4,055,625 | 10/1977 | Faugeras et al. | 423/262 |
| 5,230,439 | 7/1993 | Klok et al. | 220/901 |

FOREIGN PATENT DOCUMENTS

| | | | |
|---|---|---|---|
| 0270661 | 8/1989 | Germany | 23/294 R |
| 4014289 | 7/1965 | Japan | 23/294 R |
| 0102276 | 9/1978 | Japan | 23/294 R |
| 0583806 | 12/1977 | U.S.S.R. | 23/294 R |

*Primary Examiner*—Hezron E. Williams
*Assistant Examiner*—George M. Dombroske
*Attorney, Agent, or Firm*—Ronald O. Neerings; James C. Kesterson; Richard L. Donaldson

[57] ABSTRACT

An anhydrous ammonia gas sampler and concentration system (10) and method is disclosed that facilitates the collection and evaporation of large volumes of anhydrous ammonia in a safe, clean environment. The ammonia is collected and frozen in two containers (12, 14) connected in series and immersed in a liquid nitrogen bath (42). The frozen ammonia is evaporated through a very slow evaporation process after the containers are removed from the liquid nitrogen bath. The resultant contaminant concentrate provides the means by which a more accurate calculation of the percentage of contaminants in an ammonia sample may be made.

20 Claims, 4 Drawing Sheets

ANHYDROUS AMMONIA GAS SAMPLER AND CONCENTRATION SYSTEM

This application is a continuation of application Ser. No. 08/209,028 filed Mar. 10, 1994.

FIELD OF THE INVENTION

The present invention relates to the field of gas sampling. More specifically, the present invention relates to an anhydrous ammonia gas sampler and concentration system.

BACKGROUND OF THE INVENTION

Ammonia gas has been used in commercial and industrial environments for many years. Some applications for using ammonia are sensitive to contaminants within the ammonia. For example, semiconductor manufacturers use ammonia gas in some of their fabrication processes. Contaminants within the ammonia can adversely affect the quality and quantity of the resulting 1 semiconductor devices. Consequently, semiconductor manufacturers strive to use ammonia gas with the least amount of contamination.

Presently available testing devices and systems require hydrolyzation of the ammonia as one of the steps in testing ammonia gas for contamination. Unfortunately, there are inherent problems associated with the hydrolyzation step that interfere with the goal of detecting contamination. One problem involves the purity of the water used in the process. The water itself must be tested to make sure it has no contaminants. If contaminated water is used, the detected level of contamination of the ammonia may be inaccurate. This extra process of testing the water for contamination is expensive and time consuming. Moreover, if the water is found to contain too many contaminants, the only options are to purify the water or obtain uncontaminated water from another source. Both options involve more expense and time.

Another problem with the hydrolyzation step concerns the loss of some metallic contaminants from the sampled ammonia gas. In hydrolyzation, the ammonia gas bubbles through the water. Contaminants in the ammonia gas are suppose to dissolve into the water. Unfortunately, some of the bubbles of ammonia gas pass through the water before the contaminants can fully dissolve into the water. When the bubbles exit the water and burst, the gas, and any remaining contaminants, are released and vented to an exhaust system. The speed that the bubbles passing through the water and the loss of heat during the hydrolyzation step are major factors in the percentage of contaminants that dissolve in the water. The result is an inaccurate detected level of contamination of the ammonia gas.

Yet another problem with the hydrolyzation step is that water is saturated with ammonia at about 28% which dilutes the sample thus lowering the detection limits of the analysis. Moreover, the dilution process requires that the hydrolyzed liquid be concentrated, which increases the chance for contamination.

There remains a need for an ammonia gas sampling device or system that avoids hydrolyzation.

BRIEF DESCRIPTION OF THE DRAWINGS

The novel features believed characteristic of the invention are set forth in the appended claims. The invention itself, however, as well as other features and advantages thereof, will be best understood by reference to the detailed description, read in conjunction with the accompanying drawings, wherein:

SUMMARY OF THE INVENTION

An anhydrous ammonia gas sampler and concentration system and method that facilitates the collection and evaporation of large volumes of anhydrous ammonia in a safe, clean environment without hydrolyzation of the ammonia. The ammonia is collected, frozen, and evaporated through a very slow evaporation process. The resultant contaminant concentrate provides the means by which a more accurate calculation of the percentage of contaminants in an ammonia sample may be made.

DETAILED DESCRIPTION OF THE INVENTION

Figure 1:
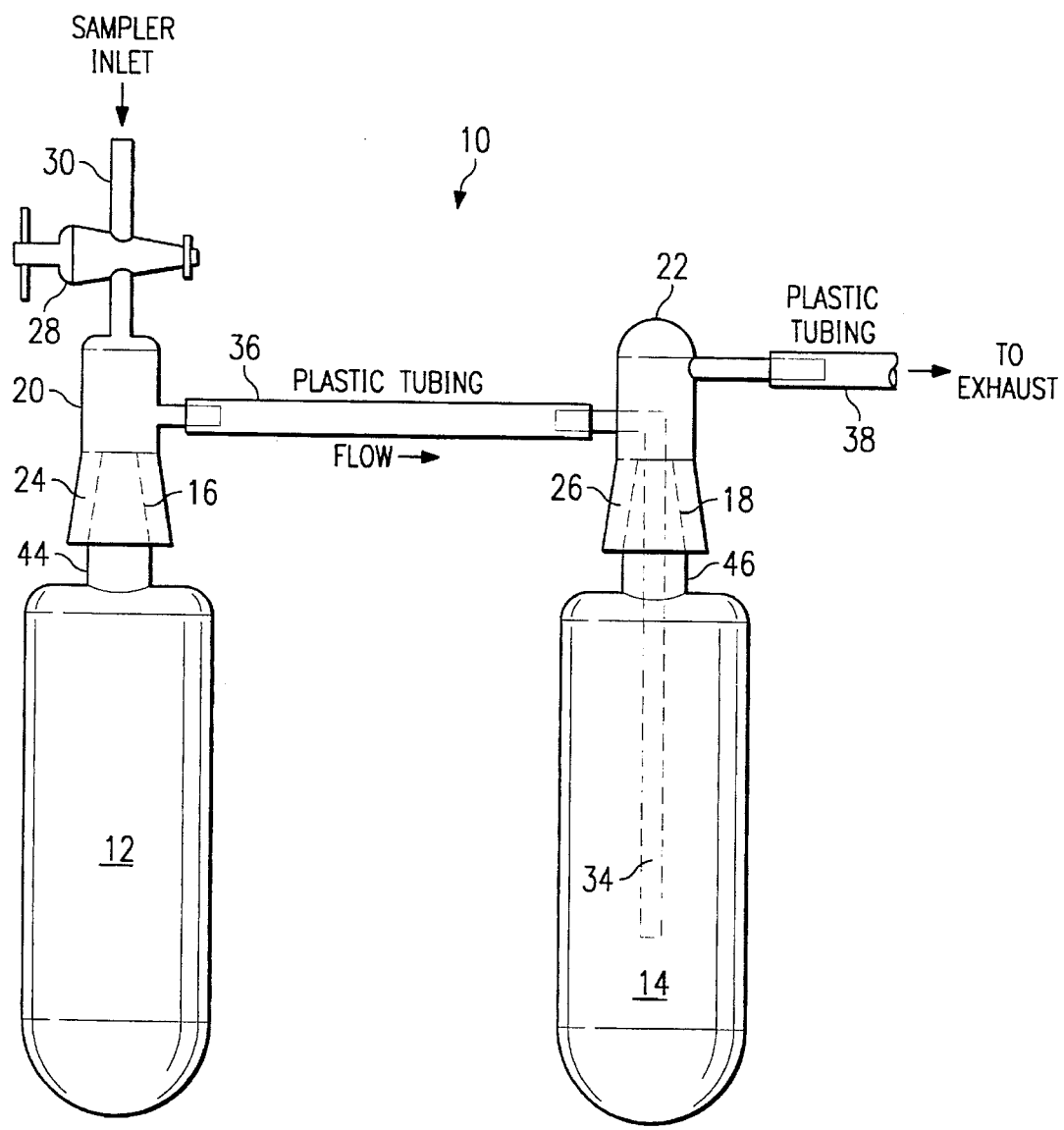
FIG. 1 illustrates an anhydrous ammonia sampler and concentration assembly 10.

FIG. 1 illustrates an anhydrous ammonia sampler and concentration assembly 10 according to one embodiment of the invention. Sample vessels 12 and 14 are identical containers each capable of holding up to 280 grams of ammonia. Quartz is used for temperature conducting reasons because it is a relatively good conductor of heat that can withstand the low temperatures of liquid nitrogen. Quartz is also used for cleanliness reasons because quartz is a high purity non-metallic material resistant to contamination. Openings in vessels 12 and 14 terminate in roughened or sand blasted taper connections 16 and 18, respectively. Vessel 12 is the primary collection vessel for the liquid ammonia. Vessel 14 is a secondary trap for excess ammonia not trapped by vessel 12.

Caps 20 and 22 are equipped with female taper receptors 24 and 36, respectively to match the taper of connectors 16 and 18. Caps 20 and 22 are also constructed of a quartz material for cleanliness reasons. Taper receptors 24 and 26 are roughened or sand blasted in the same manner as connectors 16 and 18. Cap 20 is further equipped with an integral stopcock 28 that couples cap 20 to a sampler inlet 30. Stopcock 28 has a hole that is slightly larger than the outside diameter of a plastic sampling tube 32 which can be threaded through sampler inlet 30 into vessel 12. Stopcock 28 facilitates isolation of the ammonia sample during handling. Cap 22 is equipped with an integral tube 34 used to direct any ammonia toward the bottom of overflow sample vessel 14. Caps 20 and 22 are connected by plastic tubing 36 to provide a flexible connection and easy assembly. Plastic tubing 38 connects cap 22 to an external scrubber or exhaust system and is used to direct any residual ammonia to an exhaust source for safety reasons.

Ammonia freezes at the temperature of liquid nitrogen. Anhydrous ammonia sampler and concentration assembly 10 facilitates a method wherein a sample of ammonia is collected, frozen, and evaporated through a very slow evaporation process. The resultant contaminant concentrate provides the means by which a more accurate calculation of the percentage of contaminants in an ammonia sample may be made.

Figure 2:
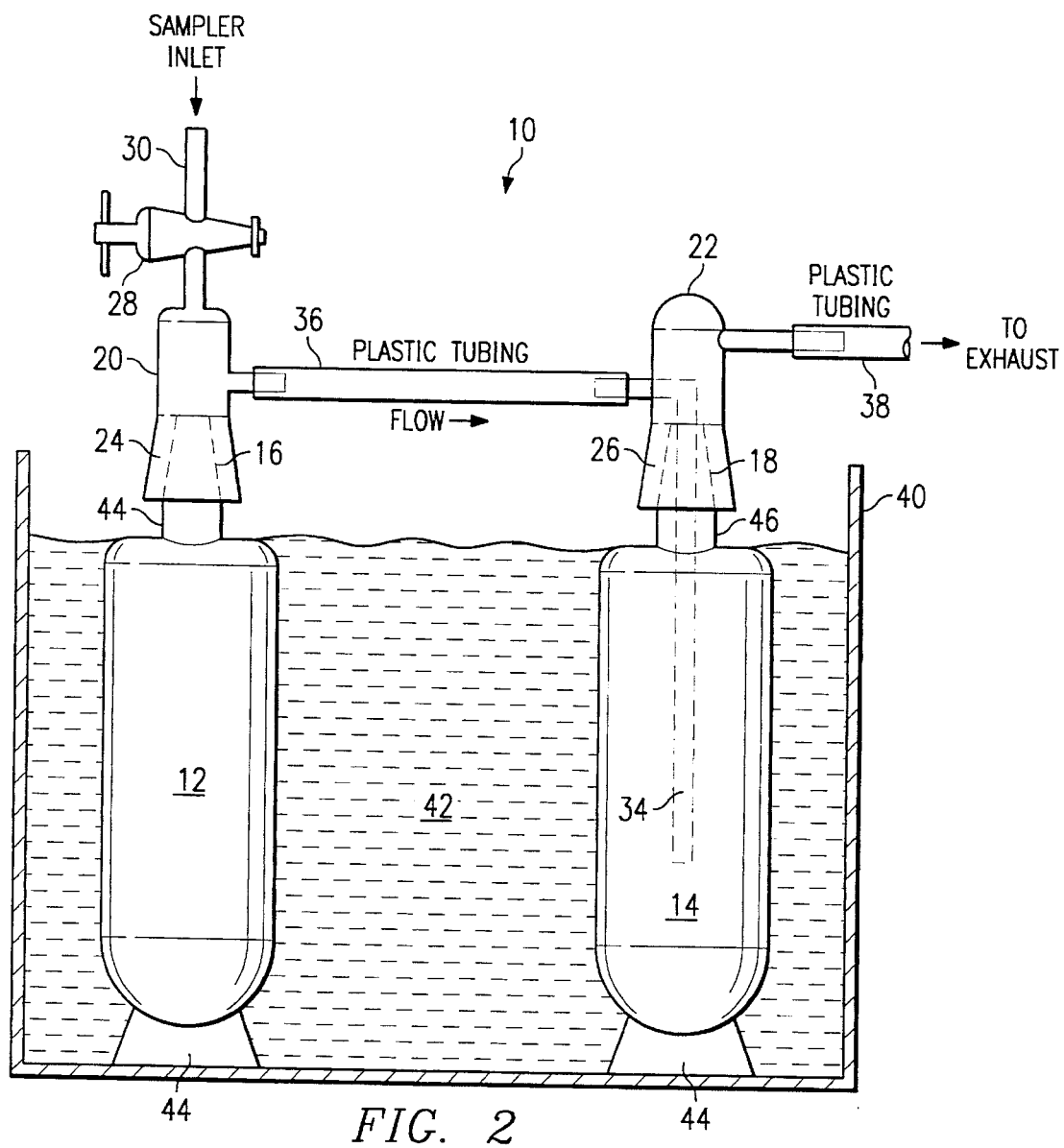
FIG. 2 illustrates an anhydrous ammonia sampler and concentration assembly 10 immersed in a tub of liquid nitrogen.
Figure 3:
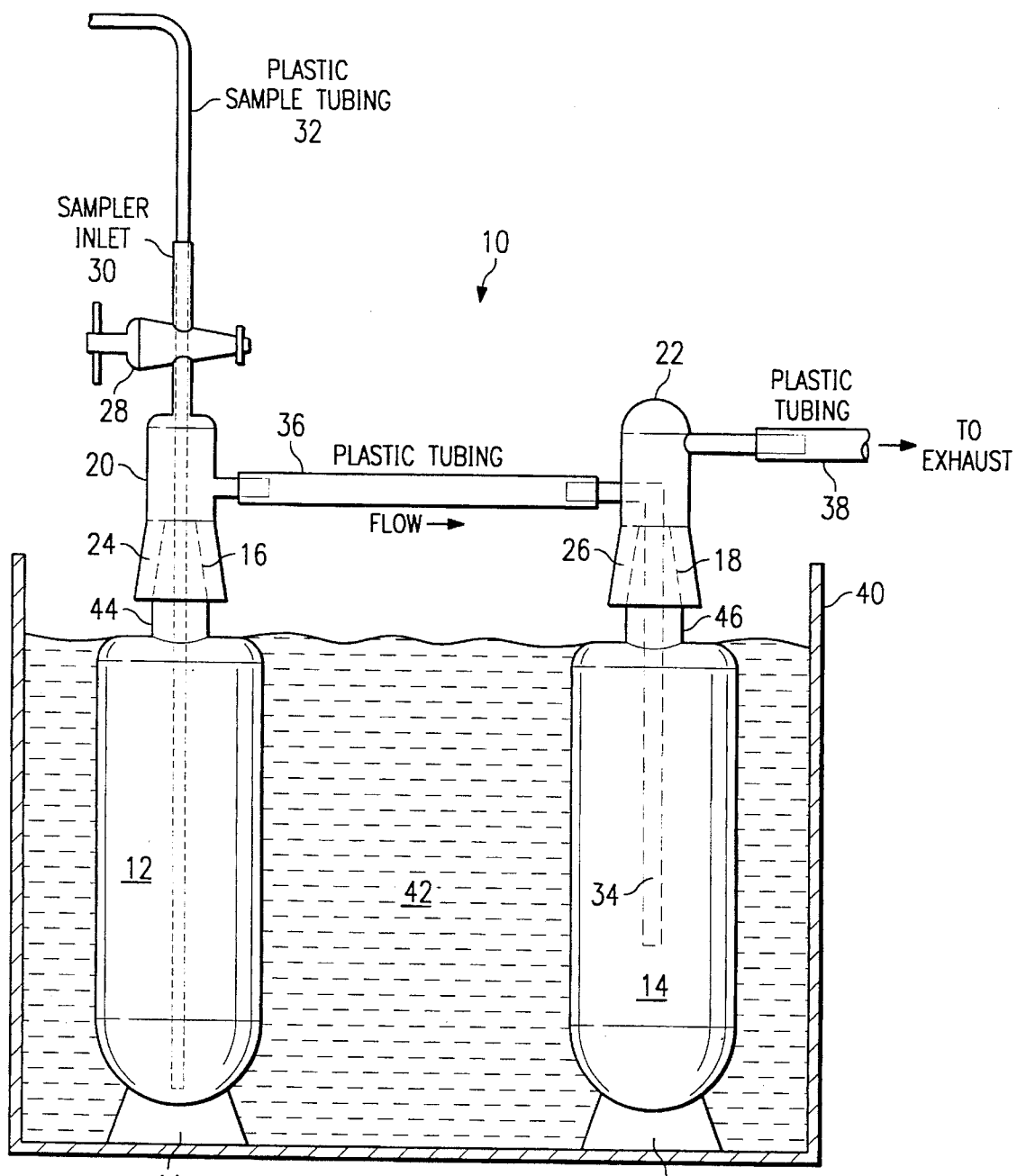
FIG. 3 illustrates an anhydrous ammonia sampler and concentration assembly 10 immersed in a tub of liquid nitrogen and further showing a sample tube for delivering ammonia from an ammonia source to a sample vessel with assembly 10.
Figure 4:
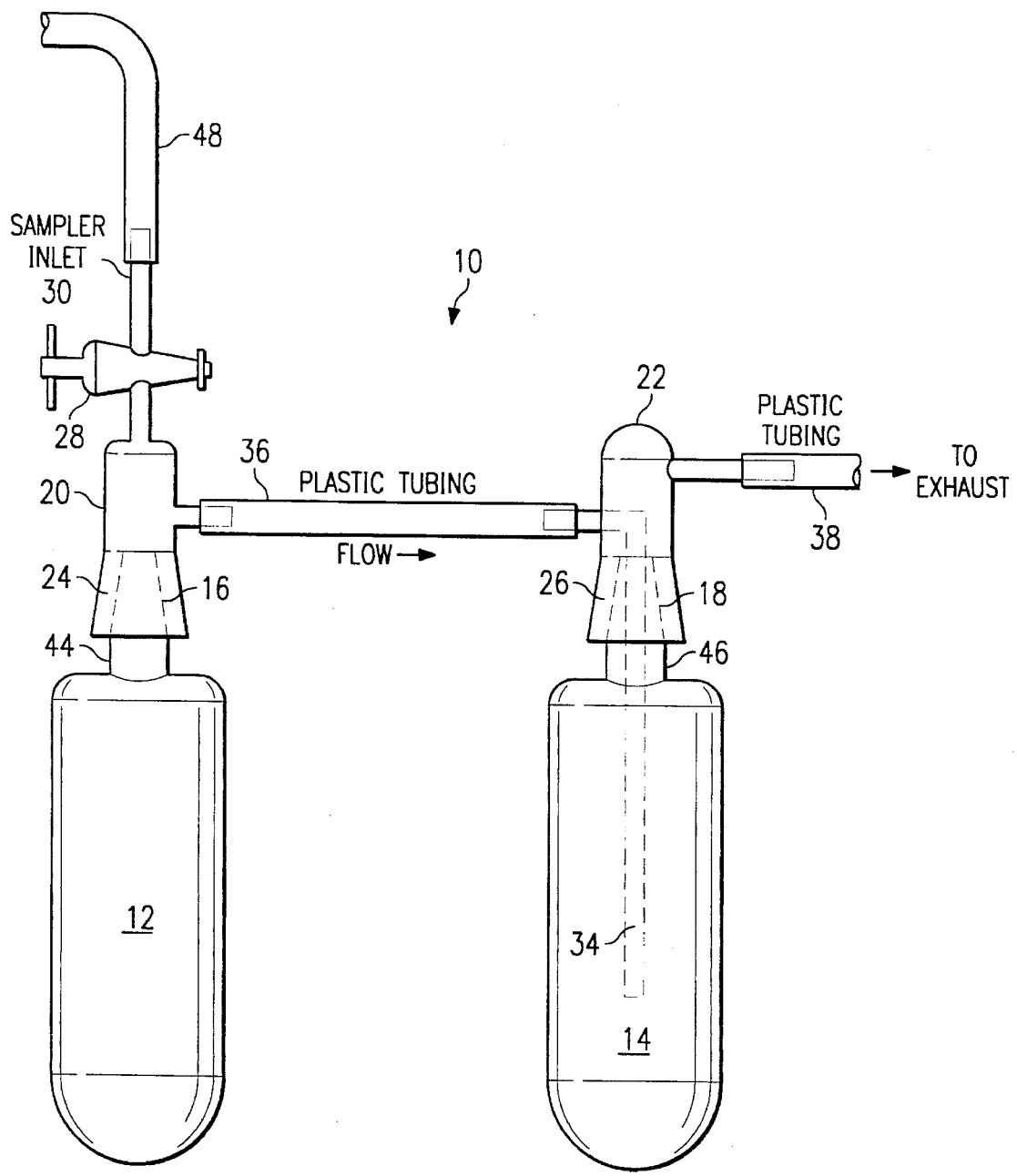
FIG. 4 illustrates an anhydrous ammonia sampler and concentration assembly 10 after removal from a tub of liquid nitrogen and further showing a tube for delivering inert gas from an inert gas source to a sample vessel with assembly 10.

FIGS. 2–4 show successive steps in a method of using anhydrous ammonia sampler and concentration system 10.

Assembly 10 is placed into a tub or tank (hood) 40 filled with liquid nitrogen 42, as shown in FIG. 2. Vessels 12 and 14 should be submerged into liquid nitrogen 42 to a point where liquid nitrogen 42 is at the level of necks 44 and 46 of vessels 12 and 14, respectively. Tub or tank 40 should have supporting surfaces for vessels 12 and 14. While bottom supports 44 are shown, vessel neck or vessel gripping supports could also be used. Liquid nitrogen 42 will boil for about 10–15 seconds immediately after assembly 10 is lowered into liquid nitrogen filled tub or tank 40 while the temperature of vessels 12 and 14 equalizes with the temperature of the liquid nitrogen. It should be noted that any oxygen in the air trapped within vessels 12 and 14 will condense out and drop to the bottom of vessels 12 and 14 as the temperature within vessels 12 and 14 equalizes with the temperature of the liquid nitrogen. If the system is open to outside sources of air, any vacuum will draw in more air resulting in more condensation of oxygen. As a result, it is recommended that ammonia Sampling begin as soon as possible after the liquid nitrogen quits boiling, to minimize such condensation.

Plastic sample tube 32 has one end connected to a source of pressurized ammonia, typically a tank (not shown), and a free or unconnected end. The free or unconnected end of sample tube 32 is threaded or inserted through sampler inlet 30, through the hole in stopcock 2B and down to the bottom of vessel 12, as shown in FIG. 3. Ammonia gas under pressure turns into a liquid. The present system functions more efficiently if the ammonia delivered into vessel 12 is in a liquid form. If a tank is the source of pressurized ammonia, it should be inverted prior to sampling so that the ammonia flowing into vessel 12 is in liquid form. Moreover, the tank should be as close to vessel 12 as possible to minimize the distance that the ammonia has to travel. The ammonia liquid is allowed to flow from its pressurized source, typically a tank, through plastic sample tube 32 and into liquid nitrogen chilled vessel 12 where it is frozen. Tube 32 is slowly withdrawn from vessel 12 as the level of ammonia rises in vessel 12. It normally takes about 30–40 seconds to fill vessel 12 with ammonia to the level of the liquid nitrogen in tub or tank 40. The flow of liquid ammonia through sample tube 32 should be stopped, using a valve on the ammonia source, before the level of ammonia in vessel 12 is above the level of the liquid nitrogen.

Most of the ammonia that flows into vessel 12 will freeze in vessel 12. Any ammonia, liquid or gas, that is not trapped in vessel 12 is directed through cap 20, tubing 36, integral tube 34 and then into the liquid nitrogen chilled sample vessel 14 where it is frozen. Any ammonia that makes it through sample vessels 12 and 14 is directed through cap 22 and tubing 38 to an independent exhaust system. Sample tube 32 is removed from cap 24 and sampler inlet 30 and stopcock 28 may be closed once the sampling process is complete.

Next, assembly 10 is removed from tub or tank 40 or liquid nitrogen 42 is removed from tub or tank 40. Assembly 10 is allowed to sit at room temperature. Heating vessels 12 and 14 is not recommended since the frozen ammonia will start to bubble and some of the contaminants will be lost in the rapid evaporation. At room temperature, the frozen ammonia within vessels 12 and 14 will slowly change from frozen ammonia into liquid ammonia which will rapidly change into ammonia gas since it is not under pressure. A gas purge line 48 connected to the source of an inert gas (nitrogen or argon for example) is connected to sampler inlet 30, as shown in FIG. 4. Stopcock valve 28 is opened and the purge gas is allowed to flow through stopcock 28, cap 20, sample vessel 12, plastic tubing 36, integral tube 34, cap 22, plastic tubing 38 and then to an independent exhaust system that preferably includes a gas scrubbing system. The gas purge (pressure should be at flow—i.e., 1 liter per minute) should be maintained for 8–12 hours or until all of the evaporating ammonia has been driven out of vessels 12 and 14.

Residue from the ammonia remains in vessels 12 and 14. The residue contains contaminants from the ammonia. Most of the metallic contaminants will be located at the bottom of vessels 12 and 14. Caps 28 and 22 are removed from vessels 12 and 14, respectively, and an acid is introduced into vessels 12 and 14 to dissolve the metal contaminants within the residue. The residue is rinsed out of vessels 12 and 14 and may now be analyzed.

Advantages of the anhydrous ammonia gas sampler and concentration of the present invention include: no fussing with hydrolyzation and associated problems and worries, improved detection limits due to large concentration factors, less accidental contamination because of a closed system (sample is under a purge during evaporation), and less losses of trace contaminants due to sample being evaporated at room temperature.

While this invention has been described with reference to an illustrative embodiment, this description is not to be construed in a limiting sense. For example, while vessels 12 and 14 and caps 20 and 22 have been described as being constructed of a quartz material for temperature conducting, safety and cleanliness reasons, any material may be used having similar characteristics. Metallic materials should typically be avoided to prevent metallic particle contamination. The size and shape of vessels 12 and 14 can changed to suit existing needs and the method of interconnecting vessels 12 and 14 to caps 20 and 22, respectively, can be changed from taper connections to other type of connection means as long the concerns of safety and cleanliness are met. Various modifications to the illustrative embodiment, as well as other embodiments of the invention will be apparent to persons skilled in the art upon reference to this description. It is therefore contemplated that the appended claims will cover any such modifications or embodiments as fall within the true scope of the invention.

What is claimed:

1. A method of separating contaminants from ammonia for analysis of the contamination of the ammonia, comprising the steps of:

injecting ammonia into a container subject to atmospheric pressure and having a temperature sufficiently low to solidify said ammonia;

subjecting said container land solidified ammonia to atmospheric pressure and ambient room temperature to facilitate evaporation of said ammonia; and venting said evaporated ammonia from said container, said contaminants remaining in said container.

2. The method of claim 1, wherein said ammonia injected into said container is liquid ammonia.

3. The method of claim 1, wherein said temperature sufficiently low to solidify said ammonia is the temperature of liquid nitrogen.

4. The method of claim 1, wherein a gas is used to purge said container during said evaporation.

5. The method of claim 4, wherein said gas in said gas purge is an inert gas.

6. The method of claim 1, further including the step of removing said contaminants from said container after said ammonia is completely evaporated and vented from said container.

7. The method of claim 1, wherein said evaporated ammonia is vented to an exhaust system.

8. A method of separating contaminants from ammonia for analysis of the contamination of the ammonia, comprising the steps of:

injecting ammonia into one of at least two connected containers subject to atmospheric pressure and having a temperature sufficiently low to solidify said ammonia;

subjecting said containers and solidified ammonia to atmospheric pressure and ambient room temperature to facilitate evaporation of said ammonia; and venting said evaporated ammonia from said containers, said contaminants remaining in said containers.

9. The method of claim 8, wherein said at least two containers are series connected.

10. The method of claim 8, wherein said ammonia injected into said one of at least two containers is liquid ammonia.

11. The method of claim 8, wherein said temperature sufficiently low to solidify said ammonia is the temperature of liquid nitrogen.

12. The method of claim 8, wherein said containers are under a gas purge during said evaporation.

13. The method of claim 12, wherein said gas in said gas purge is an inert gas.

14. The method of claim 8, further including the step of removing said contaminants from said container after said ammonia is completely evaporated and vented from said container.

15. The method of claim 8, wherein said evaporated ammonia is vented to an exhaust system.

16. An ammonia gas sampler and concentration system for separating contaminants from ammonia for analysis of the the contamination of the ammonia, comprising:

a source of ammonia;

a means for injecting ammonia from said source of ammonia into a first container subject to atmospheric pressure and having an opening;

a second container having an opening; and a means for coupling said opening of said first container through said opening of said second container and to an interior portion of said second container, said first and second containers being immersed in a liquid bath sufficiently cold to solidify said ammonia after which said containers are subjected to atmospheric pressure and ambient room temperature to evaporate said ammonia.

17. The system of claim 16, further including a means for venting evaporated ammonia from said first and second containers.

18. The system of claim 16, wherein said liquid bath is liquid nitrogen.

19. The system of claim 16, further including a means connected to said first and second containers wherein a gas is used to purge said containers during said evaporation.

20. The system of claim 19, wherein said gas in said gas purge is an inert gas.

* * * * *